United States Patent
Katnikov

(10) Patent No.: US 8,548,935 B2
(45) Date of Patent: Oct. 1, 2013

(54) PREDICTING A FUTURE PROPERTY USING REAGENTS BY MEASURING PROPERTIES AT POINTS IN TIME

(75) Inventor: Alexei Katnikov, Helsinki (FI)

(73) Assignee: Orion Diagnostica Oy, Espoo (FI)

( * ) Notice: Subject to any disclaimer, the term of this patent is extended or adjusted under 35 U.S.C. 154(b) by 542 days.

(21) Appl. No.: 12/867,635

(22) PCT Filed: Feb. 13, 2009

(86) PCT No.: PCT/FI2009/000025
§ 371 (c)(1),
(2), (4) Date: Aug. 13, 2010

(87) PCT Pub. No.: WO2009/101242
PCT Pub. Date: Aug. 20, 2009

(65) Prior Publication Data
US 2011/0016073 A1    Jan. 20, 2011

Related U.S. Application Data

(60) Provisional application No. 61/028,707, filed on Feb. 14, 2008.

(51) Int. Cl.
*G06F 17/00* (2006.01)
*G06N 5/02* (2006.01)

(52) U.S. Cl.
USPC .......................................................... 706/46

(58) Field of Classification Search
None
See application file for complete search history.

(56) References Cited

U.S. PATENT DOCUMENTS

| | | |
|---|---|---|
| 5,236,666 A | 8/1993 | Hulette et al. |
| 5,646,046 A | 7/1997 | Fischer et al. |
| 5,708,591 A | 1/1998 | Givens et al. |
| 6,031,815 A | 2/2000 | Heemskerk |
| 6,101,449 A | 8/2000 | Givens et al. |
| 6,269,313 B1 | 7/2001 | Givens et al. |
| 6,321,164 B1 | 11/2001 | Braun et al. |
| 6,429,017 B1 | 8/2002 | Toh et al. |
| 6,502,040 B2 | 12/2002 | Givens et al. |
| 6,898,532 B1 | 5/2005 | Toh et al. |

(Continued)

FOREIGN PATENT DOCUMENTS

| | | |
|---|---|---|
| DE | 29813965 UI | 12/1999 |
| DE | 10306024 B3 | 5/2004 |

(Continued)

OTHER PUBLICATIONS http://web.archive.org/web/20080110053531/http://wwwold.ece.utep.edu/research/webfuzzy/docs/kk-thesis/kk-thesis-html/node22.html, Jan. 2008.*

(Continued)

*Primary Examiner* — Jeffrey A Gaffin
*Assistant Examiner* — Li-Wu Chang
(74) *Attorney, Agent, or Firm* — Harness, Dickey & Pierce, P.L.C.

(57) ABSTRACT

A method for measuring specific substances and extracting objective information from the measurements that is especially applicable in immunoassays but can also be used in other assays which rely on affinity between binding partners. The invention overcomes problems and difficulties caused by disturbing or interfering phenomena by exploiting a mathematical algorithm which predicts the target value from a series of measurements performed during the reaction. The mathematical method of linear prediction is used for this purpose.

22 Claims, 1 Drawing Sheet

(56) References Cited

U.S. PATENT DOCUMENTS

| | | |
|---|---|---|
| 7,211,438 B2 | 5/2007 | Toh et al. |
| 7,634,451 B2 | 12/2009 | Gomer et al. |
| 2001/0053959 A1 | 12/2001 | Givens et al. |
| 2002/0010553 A1 | 1/2002 | Givens et al. |
| 2002/0019706 A1 | 2/2002 | Braun et al. |
| 2002/0146835 A1 | 10/2002 | Modzelewski et al. |
| 2002/0186363 A1* | 12/2002 | Samsoondar et al. ......... 356/39 |
| 2003/0049851 A1 | 3/2003 | Toh et al. |
| 2006/0149694 A1 | 7/2006 | Gorner et al. |
| 2008/0063628 A1* | 3/2008 | Davis et al. ................. 424/93.7 |

FOREIGN PATENT DOCUMENTS

| | | |
|---|---|---|
| RU | 2219596 | 12/2003 |
| WO | WO 97/50081 | 12/1997 |
| WO | WO-99/34208 A1 | 7/1999 |
| WO | WO9934208 A1 * | 8/1999 |
| WO | WO-02/070734 A1 | 9/2002 |

OTHER PUBLICATIONS

Patent Examination Report No. 1 issued on Mar. 8, 2013 by IP Australia for related Australian Patent Application No. 2009213995 (published as AU 2009213995).

First Office Action issued on Jan. 5, 2012 by the State Intellectual Property Office for related Chinese Patent Application No. 200980105391.0 (published as CN 101946169).

Second Office Action issued on Aug. 27, 2012 by the State Intellectual Property Office for related Chinese Patent Application No. 200980105391.0 (published as CN 101946169).

Search Report dated Jun. 24, 2008 issued by the UK Intellectual Property Office in United Kingdom Patent Application No. GB0803092.6.

Office Action issued on Jan. 30, 2013 by the Russian Patent Office in Russian Patent Application No. 2010137983/28(054134) (published as RU 2010137983).

* cited by examiner

PREDICTING A FUTURE PROPERTY USING REAGENTS BY MEASURING PROPERTIES AT POINTS IN TIME

The present invention relates to a method of measuring properties of a system and using the measured properties to predict a future property of said system. The present invention also relates to a computer program and to a computer readable storage medium.

The term "measured property" is understood here as being either a directly measured property or an indirectly measured property i.e. computationally or physically produced from directly measured properties.

The method has special applicability in the field of immunoassays but can also be used in other assays which rely on affinity between binding partners. More particularly the invention concerns a method for diagnosing analytes in a sample by exploiting a mathematical model i.e. an algorithm.

There is a continuing need for a rapid, accurate and reproducible method for the detection and quantification of various natural and artificial substances such as hormones, proteins, ligands and anti-ligands such as antibodies and antigens, and drugs.

However, most existing immunoassay methods that provide good accuracy require a relatively long time to wait for the reaction to proceed before a measurement is performed to obtain a physical property that is proportional to the amount of the analyte present. Typically, the time needed is from two minutes to a couple of hours, the needed time being dependent on the chosen assay procedure. The reaction final state property is then measured to define the property of interest such as the presence of the analyte or its concentration. Rapid and simultaneously accurate measurements cannot be performed because of incompleteness of the reaction.

Another problem is that in many cases it is unfortunately impossible to directly measure properties which carry information about the target property to be ascertained. Instead of this, data is available in which other effects (obstructive effects) interfere with the property(s) to be measured. Such interference causes significant errors in the measurement output.

It is therefore an aim of the present invention to overcome the problems and difficulties to predict a future property of a system.

According to the invention there is provided a method of predicting a future property of a system comprising one or more reagents, said reagents undergoing a process, the method comprising:

measuring a plurality of properties of said system at a plurality of points in time to generate a plurality of measurements for each property over a period of time; and predicting said future property by generating a combination of said plurality of measured properties by combining the properties using predetermined weights for each measured property for each point in time.

According to the invention there is further provided a computer program, that, when executed on a computer system, instructs a computer system to carry out the combination of said plurality of measurements using said predetermined weights thus predicting the said future property of the system. This computer program can be stored on a computer readable storage medium which can be read by the analysis system used for performing the analysis. The reading can be performed only once or alternatively prior to each analysis or prior to each reagent batch, thereby providing a means of adjusting the program according to the analysis circumstances, reagent batch, instrument version, local regulations or customer requirements.

Using the method of the invention there is no need to wait to measure the future property, for example until the end of the process or reaction. The future property can be predicted from a series of measurements performed much earlier, for example before the process finishes. In particular the use of a plurality of properties provides a more accurate prediction and can be used to neutralise the obstructive effects. It can thus be used even if the target property is different from the measured properties or if it is not possible to measure the target property during the process.

The invention is usually carried out by generating a linear combination of the plurality of measured properties. This yields effective results and is an relatively quick method.

The predetermined weights may be calculated by analysing a population of the system of one or more reagents undergoing the process with a known said future property at said plurality of points in time. A large amount of data is thus collected and used in the generation of the predetermined weights. The predetermined weights are preferably calculated by minimising the difference between the known future property and the future property predicted using said predetermined weights. This is preferably achieved by applying a least means squares method.

Each measured property may be measured at different points in time. However, it is convenient for each of the measured properties to be measured at the same plurality of points in time intervals to generate a plurality of measurements at each point in time. In this case, the predicting step conveniently comprises summing the plurality of measured properties at each point in time multiplied by said predetermined weights to generate a respective scalar product, followed by summing said scalar products.

According to the method of the invention at least one of said measured properties is the absorbance of light at a predetermined wavelength.

The method of the invention may be used in particular to predict the future property of a system comprising an analyte and a binding substance.

Although the system can be used to predict the future property at any time in the future it is most often, and most accurately used to predict a property of a system when the process is complete.

The measured properties can be any known physical property such as the absorbance of light at one, or a plurality of predetermined wavelengths, reflectance, light scattering, fluorescence, radioactivity, luminescence, phosphorescence, magnetism, temperature, electric conductance and electric resistance. Similarly the property to be predicted can be any physical property.

This method is primarily used in conjunction with bodily fluids such as whole blood, serum, plasma, spinal fluid, ascites fluid, urine, saliva, semen or clinical and non-clinical hygiene samples such as food, milk, sterility controls swipes from surfaces or water.

The method may further be used to predict a future quantity of a product of the process between the reagents. The quantity of the product can be calculated from the predicted future property. This enables users to, for example predict the amount of product of a reaction early on in the reaction without needing to wait for the reaction.

The use of the method is not limited by the nature of the analyzer instrument, it can be a simple hand-held (point-of-care, POC or point-of-use, POU) instrument used for single measurements in doctor's offices and small laboratories or a large automatic analyzer used in an institutional environment.

The method is especially applicable e.g. in turbidimetric and nephelometric assays.

The use of said algorithm enables certain advantageous features which facilitates the performance of the assay procedure. Those advantageous features may be for example features which correct the initial measurement, correct the temperature and humidity (either by adjusting the temperature and/or humidity to the one requested or by exploiting a correcting factor which adjust the obtained measurement to be related to a desired optimal temperature and/or humidity), degradation of reagents, compensates for individual sample stirring or shaking characteristics, enhances the assay procedure by adjusting the test result of a short measurement time to reflect the result of a longer measurement time.

Typically said method is applicable when there is a need to predict a future property of an immunological reaction. Said reaction may for example comprise a reaction between a ligand and an anti-ligand or any binding substance, preferably an antibody and antigen. Most preferably the method is applicable in an immunoassay where, usually, one or the other of ligand or anti-ligand is coated to a solid support. Such a solid support may for example be a microtiter plate, any particle, e.g. colourless latex, coloured latex, gold sol, magnetic particle, fluorescent particle.

The method of the present invention is exploitable regardless of the colour or wavelength, e.g. absorbance of any colour or wavelength between approximately 300 to 1100 nm can be used, preferably the wavelength is between 400 and 970 nm.

DRAWINGS

The invention will now be described by way of non-limitative example with reference to the accompanying drawings in which.

First a discussion of the principles behind the method will be given.

Let us denote x as the target scalar non-kinetic value or future property to be predicted. It can be a property of the reaction final state or any other objective parameter of interest.

Constructive property r is a reaction property linearly proportional to the target scalar value to be predicted. The constructive property can be kinetic, i.e. it can depend on time, $r=r(t)$.

As a rule, the constructive property is unavailable for measurements.

Obstructive property z is an observable process property that is unrelated to the target scalar value. The obstructive property can be kinetic, i.e. it can depend on time, $z=z(t)$. The obstructive property is also unavailable for measurements.

Suppose y is the property which can actually be measured. The measured property is a sum of the constructive property and the obstructive property, $$y=y(t)=r(t)+z(t).$$

It can be for instance light absorption of the binding substance measured in a certain wavelength of light.

In more complex systems, an m-dimensional vector of properties is measured. The result of measuring the properties is thus a plurality of measurements, y, as shown in M2 of FIG. 1:

$$y = \begin{bmatrix} y_1 \\ y_2 \\ \vdots \\ y_m \end{bmatrix},$$

which is a sum of constructive vector property and obstructive vector property, $$y = r + z, r = \begin{bmatrix} r_1 \\ r_2 \\ \vdots \\ r_m \end{bmatrix}, z = \begin{bmatrix} z_1 \\ z_2 \\ \vdots \\ z_m \end{bmatrix}.$$

These can be for instance light absorption values of the binding substance measured on a set of m optical spectrum points.

The problem is in that the constructive kinetic property is not available for straight measurements or it is hidden because only its entirety with the obstructive kinetic property can be actually measured. The problem cannot be solved by subtracting the obstructive kinetic property from the measured property because the obstructive property is also unavailable for measurement.

Figure 1:
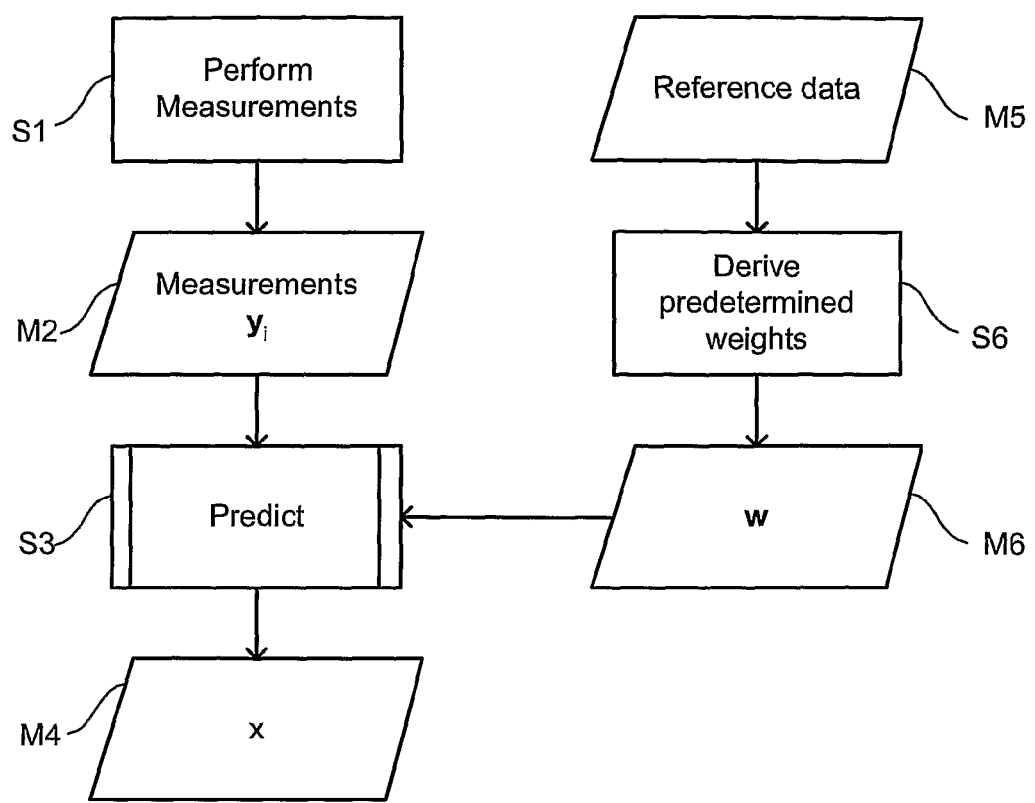
FIG. 1 is a flow diagram depicting a method of the invention.

The method shown in FIG. 1 provides processing the measured kinetic property in the way that leads to neutralizing (destroying) the obstructive property and gathering the target scalar value from the kinetic states measured at different time points.

In step S1, a plurality of m different properties of the system are measured on a set of n certain time points $t=t_1<t_2<\ldots<t_n$. The time points are usually spaced at equal intervals.

Representing the measurement of the jth property at the ith point in time as $y_{ij}$ after the measurements have been performed, the sequence of kinetic vector states, $y_1, y_2, \ldots, y_n$, is available for processing as shown by the data M2 in FIG. 1, where $$y_i = \begin{bmatrix} y_{i1} \\ y_{i2} \\ \vdots \\ y_{im} \end{bmatrix}, i = 1, 2, \ldots, n$$

Figure 2:
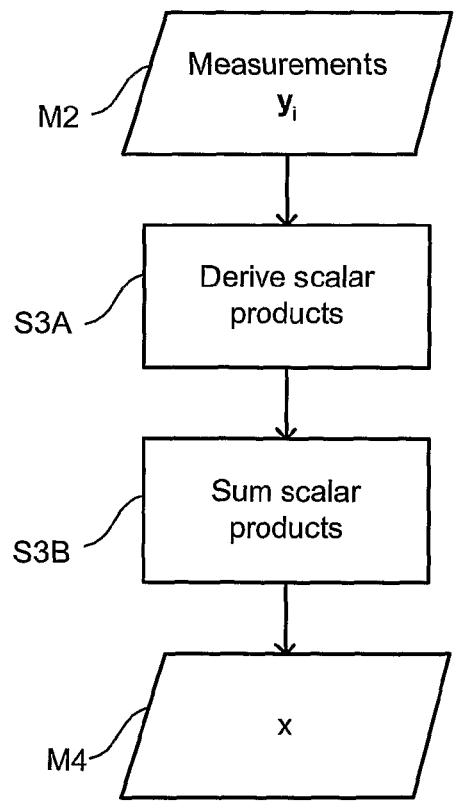
FIG. 2 depicts is a flow diagram of a method of predicting the future property.

The extracting and predicting of the target value/future property from the sequence of measured states is shown as step S3 in FIG. 1. In one embodiment, depicted in FIG. 2 it involves two processing steps.

The first step S3A is Kinetic State Scalar Mapping. Each kinetic state $y_i$ is transformed into a scalar $h_i$ which is also a sum of constructive and obstructive values in which the magnitudes and the proportion of the magnitudes are well fitted/adapted for step 2.

This operation is performed by linear summation of weighted measurements, $$h_i = \sum_{j=1}^{m} w_{ij} \cdot y_{ij}$$

where $w_{ij}$ are predefined elements of weight vectors $w_i$, $$w_i = \begin{bmatrix} w_{i1} \\ w_{i2} \\ \vdots \\ w_{im} \end{bmatrix}, i = 1, 2, \ldots, n.$$

The second step 3B is Assembling the Target. This operation neutralizes the obstructive effects and creates the target value x from the residuals.

The operation is performed by summation of the map scalars $$x = \sum_{i=1}^{n} h_i.$$

Thus the target value, x, can be predicted as shown by the data M4 in FIG. 1.

Although described in this embodiment as two distinct steps the order of the steps is not important. Thus the order of steps S3A and S3B could be reversed or alternatively a linear sum of all the measurements $y_{ij}$ multiplied by their respective predetermined weights $w_{ij}$ done in one step.

To define weight vectors $w_i$, it is convenient to concatenate them into one vector with dimension m·n, $$w = \begin{bmatrix} w_1 \\ w_2 \\ \vdots \\ w_n \end{bmatrix}.$$

Similarly, a series of kinetic states can be represented as a state vector s with the same dimension, $$s = \begin{bmatrix} y_1 \\ y_2 \\ \vdots \\ y_n \end{bmatrix}.$$

In this case the future property can be predicted by calculating the scalar product $S^T W$.

As a separate process the predetermined weights are designed, as will now be described.

Any really measured vector s is a member of the statistical population $\Omega$. Representative sample $\{s_1, s_2, \ldots, s_K\}$ from population $\Omega$ and the correspondent sample $\{x_1, x_2, \ldots, x_K\}$ of values to be predicted forms reference data, shown as the data M5 of FIG. 1. In step S6, the respective weights $w_{ij}$ are derived from the reference data M5 using the following technique. The weights are calculated using the Least Mean Squares (LSM) method which is a well known mathematical optimization technique that has been developed and discussed by many famous mathematicians (Gauss, Legendre, Laplace, Encke, Bessel, Kolmogorov, Markov). A good introduction for non-mathematicians can be found e.g. in the book: "Regression Analysis by Example, $3^{rd}$ Edition" by Samprit Chatterjee, Ali S. Hadi, Bertram Price, New York: Wiley Series in Probability and Statistics, 2000.

Consider matrix S, $$S = \begin{pmatrix} s_1^T \\ s_2^T \\ \vdots \\ s_K^T \end{pmatrix},$$

where upper index $^T$ means transpose.

Consider also K-dimensional vector x, $$x = \begin{bmatrix} x_1 \\ x_2 \\ \vdots \\ x_K \end{bmatrix}$$

Given weight vector w, operation Sw creates vector $\tilde{x}$ of predictions. Difference $\tilde{x}-x$ is the vector of prediction errors. The LMS method allows producing the weight vector w that provides the $L_2$-norm of prediction error vector $\tilde{x}-x$ as small as possible. It means minimizing the quadratic form $$\|Sw-x\|^2$$

with respect to w.

The minimization technique is well known and reduces to solving the matrix-vector equation $$Qw=b$$

where $$Q=S^TS,$$

$$b=S^Tx$$

The solution of this equation is $$w=Q^{-1}b, \tag{1}$$

where $Q^{-1}$ is the inverse of matrix Q.

Solution (1) is often very sensitive to the computational errors and to the errors of the experimental data from which matrix Q is calculated. Such sensitivity is dramatically decreased by slight modifying the matrix Q using a small tolerance coefficient r, $$w=(Q+\tau E)^{-1}b, \tag{2}$$

where E is the identity matrix.

According to the invention there is further provided a computer program, that, when executed on a computer system, instructs a computer system to carry out the combination of said plurality of measurements using said predetermined weights thus predicting the said future property of the system. This computer program can be stored on a computer readable storage medium which can be read by the analysis system used for performing the analysis. The reading can be performed only once or alternatively prior to each analysis or prior to each reagent batch, thereby providing a means of adjusting the program according to the analysis circumstances, reagent batch, instrument version, local regulations or customer requirements.

EXAMPLE

A series of CRP standard solutions having concentrations of 0, 5, 9, 19, 59, 78, 125, 151, 221, 400 and 600 mg/l were measured with a QuikRead CRP kit (Orion Diagnostica Oy, Finland) and a QuikRead 101 instrument (Orion Diagnostica Oy, Finland) according to the kit instructions.

The procedure involves a manual shaking step. Two different shaking intensities were used, a slow shaking and a vigorous shaking. The effect of shaking intensity was studied as the obstructive effect (z). Each concentration was measured with 20 replicates, 10 replicates with vigorous shaking and 10 replicates with slow shaking.

The 2-dimensional state vector (s) was measured from 20 seconds to 126 seconds spaced by 1-s intervals. The elements of measured vector state were the absorbance of red light at 653 nm wavelength and the absorbance of infrared light at 942 nm wavelength. The target parameter of interest was the absorbance of red light at 126 seconds.

The present invention was applied to predict the target parameter from the states measured within the time interval 20-66 s. The target parameter, i.e. absorbance at 653 nm at 126 seconds, was also actually measured.

The target parameter was almost insensitive to shaking intensity because 126 s measuring time is long enough for the reaction to be complete enough whereas the absorption values (y) measured during the first minute showed high dependence on shaking intensity.

The prediction weights (w) were produced in accordance with the present invention using a statistical sample comprising more than 1000 measurements.

The prediction weights (w) were then used to predict the target parameter from measurements done on solutions with known concentrations of CRP.

A standard curve using best-fit polynomials was constructed with the known CRP concentrations on one axis and the mean of measured target parameters, i.e. absorbances at 653 nm at 126 s, on the other axis. Another standard curve using best-fit polynomials was constructed with known CRP concentrations on one axis and the mean of predicted target parameters, generated from data between 20 and 66 s, on the other axis. For comparison, a third standard curve using best-fit polynomials was constructed with the known CRP concentrations on one axis and the mean of absorbances at 653 nm at 66 s on the other axis.

The concentrations of the individual replicates were then read from the corresponding standard curves. The statistics of results is shown in Table 1 and Table 2. In the data both the slow shaking and vigorous shaking results are combined. The lowering of mean square errors and coefficients of variance when the algorithm is used shows the advantageous effect of the algorithm. The mean square concentration errors based on predicted absorbances that are generated from time interval 20-66 s are smaller than the mean square concentration errors based on absorbances measured at 126 s and much smaller than those measured at 66 s. The same fact can be seen from coefficients of variance.

TABLE 1

Mean square errors (MSE), mg/l

| | with algorithm | without algorithm | |
|---|---|---|---|
| Conc., mg/l | MSE of prediction | MSE at 66 s | MSE at 126 s |
| 0 | 5.8 | 7.4 | 6.0 |
| 6 | 3.2 | 4.3 | 3.5 |
| 11 | 2.6 | 3.7 | 3.1 |
| 19 | 1.9 | 2.6 | 2.1 |
| 48 | 4.4 | 4.8 | 4.4 |

TABLE 2

Coefficient of variance (CV), %

| | with algorithm | without algorithm | |
|---|---|---|---|
| Conc., mg/l | CV of prediction | CV at 66 s | CV at 126 s |
| 6 | 54.1 | 72.1 | 58.0 |
| 11 | 23.7 | 33.7 | 27.9 |
| 19 | 10.0 | 13.8 | 11.2 |
| 48 | 9.2 | 10.0 | 9.1 |

Thus, the present invention has in this example the double advantage of providing more precise results in about half the time. The time advantage can vary on other practical setups.

The invention claimed is:

1. A method of predicting a future property of a system comprising one or more reagents, said reagents undergoing a process, the method comprising:
    measuring a plurality of properties of said system at a plurality of points in time to generate a plurality of measurements for each property over a period of time; and
    predicting said future property by generating a combination of said plurality of measured properties by combining said properties using predetermined weights for each measured property for each point in time, wherein said predicting comprises summing said plurality of measured properties multiplied by said predetermined weights at each point in time to generate a respective scalar product at each point in time, followed by summing said scalar products, wherein the method further comprises calculating said predetermined weights by analyzing a population of said system of said one or more reagents undergoing said process with a known said future property at said plurality of points in time and measurements of said properties from said population.

2. A method according to claim 1 wherein said combination of said plurality of measured properties is a linear combination of said plurality of measured properties.

3. A method according to claim 1 wherein said predetermined weights are calculated by minimising the difference between said known future property and the future property predicted using said predetermined weights.

4. A method according to claim 3 wherein said predetermined weights are calculated by applying a least means squares method.

5. A method according to claim 1 wherein each of said measured properties is measured at the same said plurality of point in time to generate a plurality of measurements at each point in time.

6. A method according claim 1 wherein the measured properties comprises any known physical property.

7. A method according to claim 1 wherein one of said measured properties of the system is the future property to be predicted.

8. A method according to claim 1 wherein said method predicts the future property of a system comprising an analyte and a binding substance.

9. A method according to claim 1 wherein said method predicts a future property of said system when said process is complete.

10. A method according to claim 1 wherein at least one of said measured properties is the absorbance of light at a predetermined wavelength.

11. A method according to claim 1 when said future property is the absorbance of light at a predetermined wavelength.

12. A method according to claim 1 wherein one or more products comprises a bodily fluid or hygiene sample.

13. A method of predicting a quantity of a product wherein said product is the product of said process between said reagents, said method comprising a method according to claim 1 and further comprising determining the quantity of said product from said predicted future property.

14. A method according to claim 1, wherein said process comprises an immunological reaction.

15. A method according to claim 14, wherein said immunological reaction comprises a reaction between a ligand and an anti-ligand.

16. A method according to claim 15, wherein said ligand and anti-ligand comprises an antibody and antigen.

17. A method according to claim 15, wherein either one of said ligand or anti-ligand is coupled to a solid support.

18. A method according to claim 17, wherein said solid support comprises a particle.

19. A method according to claim 18, wherein said particle comprises latex, gold sol or magnetic or fluorescent particle.

20. A method according to claim 1, wherein the method predicts the future property of a process comprising an immunological reaction occurring in a turbidimetric or nephelometric assay.

21. A non-transitory computer readable storage medium having recorded thereon program code to predict a future property of a system comprising one or more reagents undergoing a process that, when executed on a computer system, instructs a computer system to carry out the steps according to claim 1.

22. An analysing tool to predict a future property of a system comprising one or more reagents undergoing a process, the analysing tool comprising:
    means for measuring a plurality of properties of said system comprising said one or more reagents; and
    a processor configured to carry out the steps according to claim 1.

* * * * *